United States Patent [19]

Porteous et al.

[11] Patent Number: 4,617,950

[45] Date of Patent: Oct. 21, 1986

[54] GINGIVAL RETRACTION CORD WITH WET, DRIP-FREE ASTRINGENT

[75] Inventors: Don D. Porteous, Los Angeles; Paul M. Wittrock, Van Nuys, both of Calif.

[73] Assignee: Van R Dental Products, Inc., Los Angeles, Calif.

[21] Appl. No.: 725,489

[22] Filed: Apr. 22, 1985

[51] Int. Cl.⁴ .............................................. A61C 15/00
[52] U.S. Cl. ......................................... 132/91; 424/70
[58] Field of Search ...................... 132/89, 91; 424/70

[56] References Cited

U.S. PATENT DOCUMENTS

| | | | |
|---|---|---|---|
| 660,943 | 10/1900 | Bauermeister | 132/89 |
| 2,667,443 | 1/1954 | Ashton | 132/91 X |
| 2,700,636 | 1/1955 | Ashton | 132/89 X |
| 3,863,655 | 2/1975 | Smith | 132/91 |
| 4,029,113 | 6/1977 | Guyton | 132/91 |

OTHER PUBLICATIONS

Sagarin, Science and Technology, 1957, pp. 338, 343–344.

Primary Examiner—Gregory E. McNeill
Attorney, Agent, or Firm—Donald Diamond

[57] ABSTRACT

An astringent retraction cord for use in dental therapeutics is provided by coating a gingival retraction cord with an astringent gel containing an astringent salt such as aluminum potassium sulfate and a bodying agent sufficient to stiffen the salt solution to stand on the cord. The gel coated retraction cord is adapted to be inserted into the gingival sulcus to effect retraction of gingival tissue.

34 Claims, No Drawings

GINGIVAL RETRACTION CORD WITH WET, DRIP-FREE ASTRINGENT

TECHNICAL FIELD

This invention relates to astringent retraction cords that are adapted for use in gingival retraction procedures and, more particularly, to such retraction cords in which the astringent salt is pre-dissolved so as to provide immediate astringent effect in the sulcus through the cord being "wet", but which are nonetheless drip-free, non-spilling, and easy for the dentist to use. The invention further relates to methods of use and preparation of such cords, and to gel systems enabling drip-free carriage of wet or pre-dissolved astringent salt solutions atop a retraction cord carrier for immediate astringent effect in the sulcus without need for sulcus fluids penetrating the cord and then dissolving the salt after cord placement in the sulcus.

In dental therapeutics, it is often necessary to retract gingival tissue in order to prepare patients for taking impressions, setting crowns or effecting restorations. In a typical known procedure for retracting gingival tissue, a suitably dimensioned cord structure, i.e. one of appropriate size and configuration for placement in the narrow crevice between gingival tissue and the tooth, which has been treated to incorporate a therapeutic preparation having astringent, including hemostatic properties, is disposed about the tooth and packed into the gingival crevice for a limited time to effect tissue displacement. The key to effective retraction, in addition to the mechanical retraction effected by the cord, is the release onto the tissue of the astringent salt. In the past, typical astringent retraction cords have been absorbent, usually cotton cords, which are impregnated by a manufacturer with an aqueous solution of the astringent salt, which is allowed to dry before shipping the cord. The effect in the sulcus is dependent on the body fluids resolvating the impregnated salt and this is a time related process. It is generally desirable to have a minimum time for achieving retraction for comfort of the patient and economy in dental practice. Some practitioners prepare their own astringent retraction cords by dipping a suitable absorbent cord such as cotton thread or wool yarn, or a nonabsorbent cord such as surgical silk in a solution they prepare of the astringent salt. The wetted and dripping cord is daubed to blot the solution from it and carried to the patient's mouth and placed in the sulcus. This technique has the advantage of using predissolved astringent salts which are immediately available to retract the gingival tissue, but has the drawbacks of dripping onto practitioner and patient, being widely variable in dosage since there is no control of salt concentration or transported quantities from use to use, being prone to contamination unless office glassware is meticulously cleaned after use, and appearing messy and unprofessional.

An additional disadvantage of the preparation of wetted cord by the practitioner is the need for inventory maintenance of various retraction solutions or dry retraction materials. Storage of wet cord is a problem because the absorbent cords wicks medicament from the dispensing vial container unless the cord is not at all continually exposed, which makes retrieval of the cord from the container difficult.

Accordingly, despite the potential advantages of using a predissolved astringent salt, the great majority of dental practitioners use a manufactured dry cord into which an astringent has been impregnated and dried. The absorbent cord, usually cotton cord, may be in twisted, braided or other suitable form and is customarily supplied to the dental practitioner as a length of dry cord disposed in a dispensing bottle. The therapeutic preparations which have been or can be incorporated into absorbent retraction cords include, for example, racemic epinephrine hydrochloride, water soluble aluminum salts and such compounds as ferric sulfate, and zinc sulfate. For a discussion of the preparation and utilization of braided cords in gingival retraction, see U.S. Pat. No. 4,321,038 (Porteous, 1982). A procedure for preparing and utilizing twisted cords in gingival retractions is described in U.S. Pat. No. 2,991,224 (Bell, 1961).

SUMMARY OF THE INVENTION

Accordingly, the principal object of this invention is to provide a manufactured gingival retraction cord which is wet with a predissolved solution of astringent salt for immediate astringent effect in the sulcus, is available in dispensing vials, and is free of dripping and dosage nonuniformities heretofore associated with wet cords. It is another object to provide a gingival retraction cord which is both wet and drip-free. It is a further object to provide means in an astringent solution for bodying the solution against flow so that the astringent solution remains on the retraction cord without dripping as a free-standing, self-supporting coating. It is still another object to provide astringent compositions which are stable aqueous gels for use on retraction cords.

These and other objects to become apparent hereinafter are realized by provision in accordance with the invention of drip-free, astringent gingival retraction cord providing immediately available astringent effect in the sulcus without requirement of solvation by sulcus fluids, the cord comprising a suitably dimensioned cord structure, and a bodied astringent salt solution atop the cord structure. Typically, the salt solution comprises the salt, water, and bodying means adapted to stiffen the solution for maintaining itself standing atop the cord structure, e.g. the astringent solution comprises water and a water soluble iron or aluminum salt in an effective amount for gingival retraction, the solution is bodied with a small but effective amount of an aqueous gel-forming, water dispersible resin bodying agent, such as a carboxypolymethylene resin and may further comprise an effective amount of polyol gel formation adjuvant to stabilize the gel against deterioration sometimes induced by the presence of highly ionic salts in these resins.

Accordingly in a preferred embodiment, the invention the astringent retraction cord employs an astringent solution which comprises water and a water soluble iron or aluminum salt in an effective amount for gingival retraction. Typically, the salt is present in an amount from about 5.5 weight % to about 30 weight % based on the weight of the bodied astringent solution; the solution is bodied by a bodying agent present in an amount from about 1.5 weight % to about 3 weight % based on the weight of the bodied astringent solution; the bodying agent is carboxypolymethylene, the carboxypolymethylene has a molecular weight from about 1,000,000 to 4,000,000; and there is further included a polyol gel formation adjuvant in an amount sufficient to block deterioration of the bodied astringent solution gel over time, the polyol typically having from 3 to 6 carbon atoms, e.g. selected from propylene glycol, glycerol, dipropylene glycol, and sorbitol.

In these and like embodiments, the astringent salt is typically an alumium composition selected from water soluble, astringent aluminum salts such as aluminum potassium sulfate, aluminum ammonium sulfate, aluminum sulfate, aluminum chloride hydrate and mixtures thereof, or a water soluble, astringent ferric salt, e.g. one selected from ferric sulfate, ferric subsulfate solution, ferric chloride and mixtures thereof.

As noted above, the invention further contemplates provision of a gingival retraction astringent gel comprising an aqueous solution of a water soluble astringent salt in a concentration effective for gingival retraction and a small but effective amount of a bodying agent for stiffening the solution for application to the gingival tissue atop a cord, such stiffening being to a degree that the gel is self-supporting or free-standing on the cord, i.e. the gel will not drop by gravity from the cord, and will extend beyond the cord in all directions when the cord is dragged through the gel. Such gels have the compositions noted above, e.g. they include an astringent solution which comprises water and a water soluble iron or aluminum salt in an effective amount for gingival retraction, the salt being present in an amount from about 5.5 weight % to about 30 weight % based on the weight of the bodied astringent solution; the solution is bodied by a bodying agent present in an amount from about 1.5 weight % to about 3 weight % based on the weight of the bodied astringent solution; the bodying agent is carboxypolymethylene, e.g. having a molecular weight from about 1,000,000 to 4,000,000; and there may also be incorporated a polyol gel formation adjuvant in an amount sufficient to block deterioration of the bodied astringent solution gel over time, e.g. a polyol which has from 3 to 6 carbon atoms, such as one selected from propylene glycol, glycerol, dipropylene glycol, and sorbitol; the astringent salt being a water soluble, astringent alumium salt composition selected from aluminum potassium sulfate, aluminum ammonium sulfate, aluminum sulfate, aluminum chloride hydrate and mixtures thereof, or a water soluble, astringent ferric salt selected from ferric sulfate, ferric subsulfate solution, ferric chloride and mixtures thereof.

The invention further contemplates method of retracting gingival tissue including applying to the tissue an astringent predissolved in water to provide immediately available astringent effect in the sulcus and bodied so as to be drip-free.

In particular embodiments, the method of retracting gingival tissue comprises inserting into the gingival sulcus a gingival retraction cord coated with an astringent gel containing:

a major weight percent of a fluidic polyol containing from about 3 to 6 carbon atoms, from about 5.5 to about 30 weight % of an astringent salt, and from about 1.5 to about 3 weight % of carboxypolymethylene having a molecular weight from about 1,000,000 to about 4,000,000.

In the foregoing method up to about 50 wt.% of the polyol in the astringent gel can be substituted with water, and the polyol can be propylene glycol.

The invention further contemplates the method of preparation of a drip-free retraction cord providing immediate astringent effect in the sulcus including dissolving an astringent in water, bodying the resulting solution to a drip-free condition, and applying to a retraction cord, and which may further include disposing the cord in a container having a restricted cord outlet, immersing the cord in bodied astringent aqueous solution within the container, and withdrawing the cord as needed from the container through the restricted cord outlet in bodied astringent solution quantity metering relation.

In accordance with one aspect of this invention, there is provided a gingival tissue retraction cord coated with a stable astringent gel comprising:

from about 67 to about 93 wt. % of a non-toxic fluidic polyol containing from about 3 to about 6 carbon atoms, from about 5.5 to about 30 wt. % of an astringent salt, and from about 1.5 to about 3 wt. % of carbonxypolymethylene having a molecular weight from about 1,000,000 to about 4,000,000.

In accordance with a second aspect of this invention there is provided a method for retracting gingival tissue which comprises inserting into the gingival sulcus a gingival retraction cord with a stable astringent gel comprising (a) from about 67 to about 93 wt. % of a non-toxic fluidic polyol containing from about 3 to about 6 carbon atoms, (b) from about 5.5 to about 30 wt. % of an astringent salt, and (c) from about 1.5 to about 3 wt. % of carboxypolymethylene having a molecular weight from about 1,000,000 to about 4,000,000.

In accordance with a third aspect of this invention, there is provided a stable astringent gel comprising (a) from about 67 to about 93 wt. % of a non-toxic fluidic polyol containing from about 3 to about 6 carbon atoms, (b) from about 5.5 to about 30 wt. % of an astringent salt, and (c) from about 1.5 to about 3 wt. % of carboxypolymethylene having a molecular weight from about 1,000,000 to about 4,000,000.

PREFERRED MODES

The present invention affords the advantages of a wet astringent solution and the advantages of a dry astringent retraction cord, by virtue of "freezing" the wet solution into a "dry" form. i.e. a gel form which like a dry form does not drip or wick. The invention thus brings to the dental practioner a single product having the immediate astringent effect of an office wetted retraction cord but in the convenient form of a "dry" pre-prepared dispensing cord. The usefulness of the wet astringent salt is combined with the convenience of a dispenser package, the certainty of known dosage rates, the absence of dripping and wicking, freedom from cross-contamination and need for astringent salt inventories.

Suitable gels are those which form coatings, i.e. coverings of the retraction cord which remain tangible on the surface of the cord and which are stiff enough to hang on the cord against gravity and to stand up on the cord away from the cord periphery. Some astringent salt solutions when gelled may deteriorate over time depending on the individual chemistry of the salt and the bodying agent, e.g. agar agar bodied solutions have short service lives, and the use of gel adjuvants is recommended to prolong service life, i.e. additives which stabilize the gel can be used as needed.

The gel-coatable retraction cord can have any suitable structure, as for example, a monofilament, twisted, braided, foam or knitted structure and can be fabricated from natural or synthetic materials including natural or synthetic fibers or a mixture of such fibers. Illustrative fibers include cotton, rayon, silk, nylon, polyester and the like. Cotton filaments or strands heretofore extensively used in the preparation of gingival retraction cord because the cotton fiber had high fluid absorbency characteristics are not necessarily used. The absorbency characteristic which was important when solvation of the dried astringent salt by sulcus moisture fluids is no longer a determining factor in selection of fibers, since the salt is introduced into the sulcus in predissolved form, already in solution, and atop the cord ready for immediate astringency. Apart from the cord material it is contemplated that other cord properties, dead memory, strength, resistance to splitting and fraying heretofore identified will continue in the present cords, including sizing ranging from very small, to small, medium and large, with cord diameters generally being in the range from less than 0.04 cm to about 0.08 cm.

The invention gel coated retraction cord is typically prepared by drawing the non-coated retraction cord through the astringent gel described hereinafter. In an embodiment adapted for clinical use, the gel coated cord can be prepared by placing a suitable quantity of cord in a container doubling as a dispensing vial, adding the astringent gel to the vial, and capping the vial with a closure that is provided with a restrictive cord dispensing orifice which is slightly larger than the cord so as to doctor the gel coating on the cord to a predetermined coating thickness during withdrawal of the gel coated cord from the dispensing container vial. It should be noted here that the gelation of the astringent salt solution blocks wicking of the solution up the cord so that the cord tip which is exposed from the vial to facilitate pulling another length of cord does not drip, nor does the solution spill out if the container is upset.

In use the retraction cord of the invention is used as any other retraction cord, but with the added convenience and efficiency features noted herein. The dental practitioner passes the gel coated cord around the neck of the tooth and packs it into the gingival sulcus. Contact of the gel with the gingival tissue at the increased temperature in the mouth effects releases the dissolved salt from the gel by a variety of means including osmotic pressure differentials whereby the salts diffuse into the gingival tissue and effect retraction thereof by the usual process of astringency common to all retraction cord devices, only the mode of delivery, not the mode of retraction is changed by the present invention which is a further advantage to the practioner.

Typical astringent gel compositions are described in detail below. The invention however is not limited to these systems, since any bodied astringent salt which will coat onto a retraction cord is useful herein. Nonetheless presently preferred systems comprise an astringent salt and a hydrophyllic bodying agent.

Astringency is imparted to the invention cord by incorporating an astringent salt such as aluminum salt, ferric salt or the like. Illustrative aluminum salts includes aluminum postassium sulfate, aluminum ammonium sulfate, aluminum chloride hydrate and aluminum sulfate. Illustrative ferric salts include ferric sulfate, ferric chloride hydrate and ferric subsulfate solution. Appropriate mixtures of such salts can also be used to effect astringency. The astringent salt is generally present in the gel in an amount from about 5.5 to about 30 weight % and, preferably, in an amount from about 15 to about 20 weight. %, based on the weight of the bodied solution.

Bodying or gelation of the solution of the astringent salt can be obtained through the use of hydrophillic resins as, for example, Carbopol resins which are acrylic acid polymers cross-linked with a polyalkenyl polyether. Carbopol resins are available from The BF Goodrich Company as Carbopol Water Soluble Resins as described in their brochure GC-67. Carbopol resins are illustrative of various water soluble resins sold or useful as thixatropes and ugenerally identified herein as carboxypolymethylenes.

Carboxypolymethylene is generally present in the astringent gel in an amount from about 1.5 to about 3 weight. % and, preferably in an amount from about 1.75 to about 2.25 weight. %. Useful carboxypolymethylene resin generally has molecular weight from about 1,000,000 to about 4,000,000 and, preferably, has a molecular weight from about 2,500,000 to about 3,500,00. The carboxyl content of the carboxypolymethylene resin is advantageously from about 56 to about 64 wt. %, with the carboxyl content of Carbopol resins being about 62.5 wt. %.

In one aspect of the invention, stability of gelled astringent solutions is increased with the use of a gel adjuvant, particularly a fluidic polyol. The term "fluidic polyol" as used herein refers to polyols that are normally liquid under ambient conditions or which are combined with water to be fluid. The fluidic polyols herein are non-toxic compounds having from about 3 to about 6 carbon atoms. Illustrative polyols include propylene glycol, glycerol, and dipropylene glycol as well as sorbitol in aqueous solution from such as 70% aqueous sorbitol. The polyol adjuvant is generally employed in at least a gel stabilizing amount, e.g. above about 5 weight %, based on the weight of the bodied solution, but can be used in major weight amounts in lieu of the more expensive resins, e.g. in amounts from about 73 to about 83 wt. % of which up to about 50 weight % of the polyol adjuvant may be water rather than polyol per se.

The astringent gel according to the invention is prepared by dissolving the astringent salt in water, suitably in the polyol adjuvant, with agitation and then adding the water soluble bodying agent gelling resin thereto with continued agitation to obtain a dispersion of the resin, with the amount of each ingredient in the mix being within the concentration range as hereinabove set forth. Illustrative mixing techniques and equipment which can be used in preparing the gel are described in the aforementioned BF Goodrich brochure. Upon completion of the mixing procedure, there is obtained a stable, cord coatable, astringent gel.

EXAMPLES

The following examples further illustrate the invention. The gelling agent used in the examples is identified as Carbopol 934P. Carbopol is the trademark of The BF Goodrich Company for carboxypolymethylene resins (acrylic acid polymers) and 934P designates a particular carboxypolymethylene resin having a molecular weight of approximately 3,000,000. The compositions identified in the examples were prepared in a Waring blender with the order of addition of ingredients being as follows: polyol; water, if any; astringent salt, color and flavor; and Carbopol resin. Where the weight ratio of water to polyol is not in excess of about 1 to 1, the duration of the mixing cycle is relatively short. Thickening commences upon the addition of the resin to the astringent salt solution and transformation of the gel occurs shortly thereafter. The gelation composition can be formulated with a suitable preservative, where required.

EXAMPLE I

This example illustrates a basic astringent gel wherein the solvent is water.

1A

| Composition | Wt., grams | Wt. % |
|---|---|---|
| Water | 100 | 64 |
| Aluminum potassium sulfate | 51 | 32 |
| Carbopol 934P | 6 | 4 |

1B

This example illustrates an astringent gel wherein the solvent was propylene glycol.

| Composition | Wt., grams | Wt. % |
|---|---|---|
| Propylene glycol | 200 | 78 |
| Aluminum potassium sulfate | 51 | 20 |
| Carbopol 934P | 5 | 2 |
| | 256 | 100 |

The above compositions produce a useful astringent salt gel.

EXAMPLE II

This example illustrates astringent gels wherein the solvent was a blend of water and polyol, with the weight ratio of water to polyol not exceeding 1 to 1.

2A

| Composition | Wt., grams | Wt. % |
|---|---|---|
| 70% aqueous sorbitol | 100.0 | 63.3 |
| Aluminum chloride hydrate | 15.0 | 9.5 |
| Water | 35.0 | 22.1 |
| Color | 0.5 | 0.05 |
| Flavor | 0.5 | 0.05 |
| Carbol 934P | 8.0 | 5.0 |
| | 159.0 | 100.00 |

2B

| Composition | Wt., grams | Wt. % |
|---|---|---|
| 70% aqueous sorbitol | 100.0 | 63.9 |
| Aluminum chloride hydrate | 15.0 | 9.6 |
| Water | 35.0 | 22.4 |
| Color | 0.5 | 0.3 |
| Flavor | 0.5 | 0.3 |
| Carbopol 934P | 5.5 | 3.5 |
| | 156.5 | 100.0 |

In composition 2A and 2B, the polyol was aqueous sorbitol. Composition 2A had good gel and astringency characteristics. Composition 2B had good astringency characteristics, but initially there was a slight phase separation which diminished upon standing to form a homogenous gel.

2C

| Composition | Wt., grams | Wt. % |
|---|---|---|
| Propylene glycol | 100.0 | 40.65 |
| Water | 100.0 | 40.65 |
| Aluminum potassium sulfate | 40.0 | 16.3 |
| Color | 0.5 | 0.2 |
| Flavor | 0.5 | 0.2 |
| Carbopol 934P | 5.0 | 2.0 |
| | 246.0 | 100.0 |

2D

| Composition | Wt., grams | Wt. % |
|---|---|---|
| Propylene glycol | 100.0 | 40.65 |
| Water | 100.0 | 40.65 |
| Aluminum Chloride Hydrate | 40.0 | 16.3 |
| Color | 0.5 | 0.2 |
| Flavor | 0.5 | 0.2 |
| Carbopol 934P | 5.0 | 2.0 |
| | 246.0 | 100.0 |

2E

| Composition | Wt., grams | Wt. % |
|---|---|---|
| Propylene glycol | 88.0 | 35.7 |
| Water | 112.0 | 45.5 |
| Aluminum Chloride Hydrate | 40.0 | 16.22 |
| Color | 0.6 | 0.24 |
| Flavor | 0.6 | 0.24 |
| Carbol 934P | 5.2 | 2.1 |
| | 246.4 | 100.00 |

2F

| Composition | Wt., grams | Wt. % |
|---|---|---|
| Propylene glycol | 105.0 | 39.9 |
| Water | 105.0 | 39.9 |
| Aluminum potassium sulfate | 40.0 | 15.2 |
| Trisodium Phosphate | 8.0 | 3.1 |
| Color | 0.5 | 0.2 |
| Flavor | 0.5 | 0.2 |
| Carbopol 934P | 4.0 | 1.5 |
| | 263.0 | 100.0 |

2G

| Composition | Wt., grams | Wt. % |
|---|---|---|
| Propylene glycol | 100.0 | 39.0 |
| Water | 100.0 | 39.0 |
| Aluminum potassium sulfate | 51.0 | 19.8 |
| Color | 0.5 | 0.2 |
| Flavor | 0.2 | 0.1 |
| Carbopol 934P | 5.0 | 1.9 |
| | 256.7 | 100.0 |

2H

| Composition | Wt., grams | Wt. % |
|---|---|---|
| Propylene glycol | 107.5 | 42.96 |
| Water | 87.5 | 34.96 |
| Aluminum potassium sulfate | 50.0 | 19.98 |
| Color | 0.025 | 0.01 |

-continued

| Composition | Wt., grams | Wt. % |
| --- | --- | --- |
| Flavor | 0.25 | 0.10 |
| Carbol 934P | 5.0 | 1.99 |
| | 250.275 | 100.00 |

2I

| Composition | Wt., grams | Wt. % |
| --- | --- | --- |
| Propylene glycol | 113.3 | 44.09 |
| Water | 66.7 | 26.0 |
| Aluminum potassium sulfate | 40.0 | 16.1 |
| Color | 0.6 | 0.24 |
| Carbopol 934P | 7.0 | 2.82 |
| | 248.2 | 100.00 |

In compositions 2C through 2I, the polyol was propylene glycol. These compositions had good gel and astringency characteristics, with compositions 2C, 2D, and 2G-I being preferred for homogeneity of gel.

2J

| Composition | Wt., grams | Wt. % |
| --- | --- | --- |
| Glycerol | 100.0 | 40.3 |
| Water | 100.0 | 40.3 |
| Aluminum potassium sulfate | 40.0 | 16.1 |
| Color | 0.6 | 0.24 |
| Flavor | 0.6 | 0.24 |
| Carbopol 934P | 7.0 | 2.82 |
| | 248.2 | 100.00 |

In composition 2J, the polyol was glycerol. This composition had good astringency characteristics.

EXAMPLE III

Small and medium size braided retraction cords were coated with a bodied astringent solution or gel of Example 2F and evaluated by clinical investigators for effectiveness in gingival retractions. The small, braided retraction cord had four warp strands, four filling strands, fifty two picks or plaits per linear inch, a diameter of about 0.5 mm (0.02 in.), and utilized No. 60/2 cotton thread for all strands. The medium, braided retraction cord, which utilized No. 60/2 cotton thread for the axial support strands, had four warp strands, three axial support strands, four filling strands, thirty eight picks or plaits per linear inch, and a diameter of about 0.635 mm (0.025 in). The cords were placed in dispensing vials which were then loaded with astringent gel corresponding to Composition 2F and the vials were capped with a cord dispensing closure. The clinical investigators reported that the gel coated cord of this invention offers significant advantages to the dental practitioner in the retraction of the gingival tissue. It was noted that the wet cord made intimate contact immediately with the wet mouth tissue, unlike dry cords; that the cord was more easily accurately placed than dry cords since the wetted nature of the cord enhanced its dead memory characteristic, and that added water e.g. via a syringe into the sulcus could be used to increase ambient moisture, all of which are further advantages resulting from the present invention.

In view of the foregoing description and examples, it will become apparent to those of ordinary skill in the art that equivalent modifications thereof may be made without departing from the spirit and scope of this invention which is to be limited solely by the following claims.

We claim:

1. Drip-free, astringent gingival retraction cord providing immediately available astringent effect in the sulcus without requirement of solvation by sulcus liquids, the cord comprising a suitably dimensioned cord structure, and a bodied astringent salt solution atop the cord structure.

2. The astringent retraction cord according to claim 1, in which the salt solution comprises the salt, water, and bodying means adapted to stiffen the solution for maintaining itself atop the cord structure.

3. The astringent retraction cord according to claim 1, in which the astringent solution comprises water and a water soluble iron or aluminum salt in an effective amount for gingival retraction.

4. The astringent retraction cord according to claim 1, in which the solution is bodied with a small but effective amount of an aqueous gel-forming, water dispersible resin bodying agent.

5. The astringent retraction cord according to claim 4 in which the water dispersible resin is a carboxypolymethylene resin.

6. The astringent retraction cord according to claim 5, including also an effective amount of polyol gel formation adjuvant.

7. The astringent retraction cord according to claim 6, in which the astringent solution comprises water and a water soluble iron or aluminum salt in an effective amount for gingival retraction.

8. The astringent retraction cord according to claim 1, in which the astringent solution comprises water and a water soluble iron or aluminum salt in an effective amount for gingival retraction.

9. The astringent retraction cord according to claim 8 in which salt is present in an amount from about 5.5 weight % to about 30 weight % based on the weight of the bodied astringent solution.

10. The astringent retraction cord according to claim 8 in which the solution is bodied by a bodying agent present in an amount from about 1.5 weight % to about 3 weight % based on the weight of the bodied astringent solution.

11. The astringent retraction cord according to claim 10, in which the bodying agent is carboxypolymethylene.

12. The astringent retraction cord according to claim 11, in which the carboxypolymethylene has a molecular weight from about 1,000,000 to 4,000,000.

13. The astringent retraction cord according to claim 12, including also a polyol gel formation adjuvant in an amount sufficient to block deterioration of the bodied astringent solution gel over time.

14. The astringent retraction cord according to claim 13 in which the polyol has from 3 to 6 carbon atoms.

15. The astringent retraction cord according to claim 14 in which the polyol is selected from propylene glycol, glycerol, dipropylene glycol, and sorbitol.

16. The astringent retraction cord according to claim 1, in which the astringent salt is an alumium composition selected from alumium potassium sulfate, alumium ammonium sulfate, aluminum sulfate, aluminum chloride hydrate and mixtures thereof.

17. The astringent retraction cord according to claim 1, in which the astringent salt is a ferric salt selected from ferric sulfate, ferric subsulfate solution, ferric chloride and mixtures thereof.

18. A gingival retraction astringent gel comprising an aqueous solution of a water soluble astringent salt in a concentration effective for gingival retraction and a small but effective amount of a bodying agent for stiffening the solution for application to the gingival tissue atop a cord.

19. The gingival retraction astringent gel according to claim 18, in which the astringent solution comprises water and a water soluble iron or aluminum salt in an effective amount for gingival retraction.

20. The gingival retraction astringent gel according to claim 19, in which the salt is present in an amount from about 5.5 weight % to about 30 weight % based on the weight of the bodied astringent solution.

21. The gingival retraction astringent gel according to claim 20 in which the solution is bodied by a bodying agent present in an amount from about 1.5 weight % to about 3 weight % based on the weight of the bodied astringent solution.

22. The gingival retraction astringent gel according to claim 21, in which the bodying agent is carboxypolymethylene.

23. The gingival retraction astringent gel according to claim 22, in which the carboxypolymethylene has a molecular weight from about 1,000,000 to 4,000,000.

24. The gingival astringent gel according to claim 21, including also a polyol gel formation adjuvant in an amount sufficient to block deterioration of the bodied astringent solution gel over time.

25. The gingival astringent gel according to claim 24 in which the polyol has from 3 to 6 carbon atoms.

26. The gingival astringent gel according to claim 25 in which the polyol is selected from propylene glycol, glycerol, dipropylene glycol, and sorbitol.

27. The gingival astringent gel according to claim 26, in which the astringent salt is an alumium composition selected from alumium potassium sulfate, alumium ammonium sulfate, aluminum sulfate, aluminum chloride hydrate and mixtures thereof.

28. The gingival astringent gel according to claim 26, in which the astringent salt is a ferric salt selected from ferric sulfate, ferric subsulfate solution, ferric chloride and mixtures thereof.

29. Method of retracting gingival tissue including applying to the tissue an astringent predissolved in water to provide immediately available astringent effect in the sulcus and bodied so as to be drip-free.

30. A method for retracting gingival tissue which comprises inserting into the gingival sulcus a gingival retraction cord coated with an astringent gel containing:
   a major weight percent of a fluidic polyol containing from about 3 to about 6 carbon atoms,
   from about 5.5 to about 30 weight % of an astringent salt, and
   from about 1.5 to about 3 weight % of carboxypolymethylene having a molecular weight from about 1,000,000 to about 4,000,000.

31. The method according to claim 30, including also maintaining water in the fluidic polyol in an amount up to about 50 weight % of the polyol.

32. The method according to claim 31, including also selecting as the polyol propylene glycol.

33. Method of preparation of a drip-free astringent retraction cord providing immediate astringent effect in the sulcus, including dissolving an astringent in water, bodying the resulting solution to a drip-free condition, and applying the bodied solution to a retraction cord structure.

34. The method of preparation of a drip-free retraction cord according to claim 33, including also disposing the cord structure in a container having a restricted outlet, immersing the cord in bodied astringent aqueous solution within the container, and withdrawing the cord as needed from the container through the restricted cord outlet in bodied astringent solution quantity metering relation.

* * * * *